US012569167B2

(12) United States Patent
Yang et al.

(10) Patent No.: US 12,569,167 B2
(45) Date of Patent: Mar. 10, 2026

(54) APPARATUS AND METHOD FOR MEASURING BLOOD GLUCOSE LEVEL

(71) Applicant: Electronics and Telecommunications Research Institute, Daejeon (KR)

(72) Inventors: Hoe Sung Yang, Daejeon (KR); Kang Bok Lee, Daejeon (KR); Kwang Soo Cho, Daejeon (KR); Kyu Won Han, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 1179 days.

(21) Appl. No.: 17/103,218

(22) Filed: Nov. 24, 2020

(65) Prior Publication Data

US 2021/0153788 A1 May 27, 2021

(30) Foreign Application Priority Data

Nov. 25, 2019 (KR) ........................ 10-2019-0152379

(51) Int. Cl.
*A61B 5/145* (2006.01)
*A61B 5/00* (2006.01)

(52) U.S. Cl.
CPC ........ *A61B 5/14532* (2013.01); *A61B 5/0059* (2013.01); *A61B 5/6833* (2013.01); *A61B 5/685* (2013.01)

(58) Field of Classification Search
CPC . A61B 5/14532; A61B 5/0059; A61B 5/6833; A61B 5/685
See application file for complete search history.

(56) References Cited

U.S. PATENT DOCUMENTS 8,169,006 B2 5/2012 Kim et al.
8,306,593 B2 11/2012 Hwang et al.
(Continued)

FOREIGN PATENT DOCUMENTS

KR 10-0694598 3/2007
KR 10-2011-0003684 1/2011
(Continued)

OTHER PUBLICATIONS

Chen et al. "Role of advanced glycation end products in mobility and considerations in possible dietary and nutritional intervention strategies" (Year: 2018).*

*Primary Examiner* — Christian Jang
(74) *Attorney, Agent, or Firm* — KILE PARK REED & HOUTTEMAN PLLC

(57) ABSTRACT

Disclosed are an apparatus and a method for measuring a blood glucose level. In the blood glucose level measurement apparatus and method, the apparatus coupled to a patch with a microneedle formed in at least one area and configured to calculate a blood glucose level of a body fluid extracted from a user may calculate the blood glucose level by analyzing a reflected light beam reflected from the patch with a microneedle formed in a second area and correct the calculated blood glucose level of the user by analyzing data obtained by measuring a reflected light beam from a first area from which the body fluid is not extracted so as to measure a precise blood glucose level with an error being reduced in consideration of environmental factors influencing measurement.

13 Claims, 11 Drawing Sheets

(56)            References Cited

U.S. PATENT DOCUMENTS

| | | | |
|---|---|---|---|
| 8,814,808 | B2 | 8/2014 | Calasso et al. |
| 8,845,078 | B2 | 9/2014 | Owaki |
| 10,251,584 | B2 | 4/2019 | Jin et al. |
| 10,779,755 | B2 | 9/2020 | Jun et al. |
| 2007/0191696 | A1* | 8/2007 | Mischler ............. G01N 21/552 600/347 |
| 2009/0163874 | A1* | 6/2009 | Krag ................ A61M 5/14248 604/180 |
| 2009/0264719 | A1* | 10/2009 | Markle ............. A61B 5/14542 600/366 |
| 2010/0141280 | A1 | 6/2010 | Yang et al. |
| 2010/0208159 | A1* | 8/2010 | Oan .................... G02B 6/0091 362/97.1 |
| 2010/0324383 | A1* | 12/2010 | Epstein ............. A61B 5/14546 600/316 |
| 2013/0197333 | A1* | 8/2013 | Petisce ................ A61B 5/4839 600/347 |
| 2018/0160908 | A1 | 6/2018 | Kim et al. |

FOREIGN PATENT DOCUMENTS

| | | |
|---|---|---|
| KR | 10-2011-0037137 | 4/2011 |
| KR | 10-1661287 | 9/2016 |
| KR | 10-1712031 | 3/2017 |
| KR | 10-2018-0097370 | 8/2018 |
| KR | 10-2019-0048706 | 5/2019 |
| KR | 10-2019-0068500 | 6/2019 |
| WO | 2017/060746 | 4/2017 |

* cited by examiner

5000

CONVEX COUPLING
STRUCTURE B

CONCAVE COUPLING
STRUCTURE G

1000

$A_1$

1500

$A_2$

APPARATUS AND METHOD FOR MEASURING BLOOD GLUCOSE LEVEL

CLAIM FOR PRIORITY

This application claims priority to Korean Patent Application No. 10-2019-0152379 filed on Nov. 25, 2019 in the Korean Intellectual Property Office (KIPO), the entire contents of which are hereby incorporated by reference.

BACKGROUND

1. Technical Field

Example embodiments of the present invention relate in general to an apparatus and a method for measuring a blood glucose level, and more particularly, to an apparatus and a method for measuring a blood glucose level in which light reflected from an area of a patch, from which a body fluid is not collected, is utilized as a correction value for calculating a blood glucose level and adhesion between the patch and the apparatus is enhanced so as to analyze a precise blood glucose level.

2. Related Art

A blood glucose level is a numerical value which indicates concentration of glucose included in a body fluid. Here, glucose is a source material which generates energy for maintaining a normal physical activity function and which temporarily increases after a meal but decreases due to insulin working so as to maintain homeostasis.

Generally, a normal range of blood glucose level exists within a range from 70 to 130 mg/dL before a meal and exists within a range of 180 mg/dL after a meal.

Meanwhile, when a blood glucose level exceeds the normal range, the blood glucose level is classified into hyperglycemia. On the other hand, when a blood glucose level is less than the normal range, the blood glucose level is classified into hypoglycemia.

Hyperglycemia acts as a cause of diabetes. In the case of diabetes, since glucose in a body fluid is discharged through urine, complications such as cardiac arrest, a stroke, acute renal failure, retinopathy, diabetic neuropathy, and the like are caused due to lack of energy and hypoglycemia causes symptoms such as unconsciousness and brain damage and leads up to death in severe cases. Accordingly, to prevent risks caused by hyperglycemia and hypoglycemia, it is very important to consistently maintain a blood glucose level within the normal range.

Hence, autonomously measurable blood glucose level measurement apparatuses have been provided hitherto.

Generally, conventional blood glucose level measurement apparatuses measure a blood glucose level using a collecting method. However, in the case of conventional blood glucose level measurement apparatuses using the collecting method, a body fluid is obtained by pricking a fingertip with a sterilized needle or the like and the body fluid is analyzed to measure a blood glucose level in the body fluid.

However, conventional blood glucose level measurement apparatuses using the collecting method have a disadvantage of causing pain and fear to users.

Accordingly, as shown in FIG. 1, a blood glucose level measurement apparatus is provided that is configured to attach a patch including a microneedle to the skin and measure a change in an enzyme in the patch using a light source control module so as to relieve causing pain and fear to users.

However, in the case of the conventional blood glucose level measurement apparatus shown in FIG. 1, since the patch is poorly pressed against the light source control module while a wavelength and an intensity level of reflected light reflected from the patch are measured using the light source control module, an error occurs in measuring a blood glucose level.

SUMMARY

Accordingly, example embodiments of the present invention are provided to substantially obviate one or more problems due to limitations and disadvantages of the related art.

Example embodiments of the present invention provide a blood glucose level measurement apparatus having high precision, high efficiency, and high convenience.

Example embodiments of the present invention also provide a blood glucose level measurement method having high precision, high efficiency, and high convenience.

In some example embodiments, a blood glucose level measurement apparatus bound to a patch including at least one microneedle formed on one surface and including at least one enzyme configured to react with a body fluid of a user so as to measure a blood glucose level in the extracted body fluid using the patch includes light sources configured to emit light toward the other surface of the patch, a photodetector configured to receive the light received by the enzyme which reacts with the body fluid, and a case configured to accommodate the light sources and the photodetector. Here, the apparatus is bound to the patch through an uneven structure formed on the other surface of the patch and one surface of the case.

The enzyme may react with glycation products in the body fluid and may generate advanced glycation endproducts (AGEs).

The uneven structure may be formed by at least one fixing protrusion and at least one fixing groove, and a height of the fixing protrusion may correspond to a depth of the fixing groove.

The at least one fixing protrusion may be formed on the other surface of the patch, and the at least one fixing groove may be formed on the one surface of the case.

The fixing protrusion may be provided to have a cylindrical shape having a certain diameter, and the fixing groove may have a quadrangular frame shape with a width corresponding to the diameter of the fixing protrusion.

The fixing protrusion and the fixing groove may have quadrangular frame shapes with certain widths.

The fixing protrusion may be provided to have a linear bar shape having a certain width, and the fixing groove may be provided to have a quadrangular frame shape with a width corresponding to a diameter of the fixing protrusion.

When a plurality of such fixing protrusions are formed to be arranged on the other surface of the patch, the fixing groove may fit on and be bound to any one of the plurality of fixing protrusions.

The at least one fixing groove may be formed on the other surface of the patch and the at least one fixing protrusion may be formed on the one surface of the case.

The fixing groove may be provided to have a quadrangular frame shape having a certain width, and the fixing protrusion may have a cylindrical shape having a diameter corresponding to the width of the fixing groove.

When a plurality of such fixing grooves are formed to be arranged on the other surface of the patch, the fixing protrusion may be inserted into and bound to any one of the plurality of fixing grooves.

The patch may include a first area in which the microneedle is not formed and a second area in which the microneedle is formed.

The photodetector may receive a first reflected light beam reflected from the first area and a second reflected light beam reflected from the second area among light beams emitted by the light sources and may measure any one of wavelengths and intensity changes of the first reflected light beam and the second reflected light beam.

The photodetector may calculate a blood glucose level by analyzing data obtained by measuring the second reflected light beam and may correct the calculated blood glucose level on the basis of a result of analyzing data obtained by measuring the first reflected light beam.

The light sources may include a first light source configured to emit light toward the first area and a second light source configured to emit light toward the second area. Here, the first light source may be located at a first point which allows a path of the first reflected light beam to face the photodetector of the apparatus, and the second light source may be located at a second point which allows a path of the second reflected light beam to face the photodetector.

In other example embodiments, a blood glucose level measurement apparatus bound to a patch including a first area and a second area, in which a microneedle is formed, and including at least one enzyme configured to react with a body fluid of a user and configured to measure a blood glucose level in the body fluid extracted from the second area using light sources and a photodetector includes a memory, and a processor configured to execute at least one instruction stored in the memory. Here, the at least one instruction includes an instruction for operating the light sources to emit light beams toward the first area and the second area, an instruction for operating the photodetector to receive a first reflected light beam reflected from the first area and a second reflected light beam reflected from the second area among the emitted light beams and measure any one of wavelengths and intensity changes of the first reflected light beam and the second reflected light beam, an instruction for analyzing data obtained by measuring the second reflected light beam and calculating a blood glucose level, and an instruction for analyzing data obtained by measuring the first reflected light beam and correcting the calculated blood glucose level on the basis of a result of analyzing.

The patch may include at least one microneedle formed on one surface and at least one fixing protrusion formed on the other surface.

The light sources and the photodetector may be accommodated in the case, and a fixing groove may be formed in one surface of the case to be bound to the other surface of the patch.

The at least one fixing groove may be formed on the other surface of the patch, and at least one fixing protrusion may be formed on one surface of a case.

In still other example embodiments, a blood glucose level measurement method using a blood glucose level measurement apparatus bound to a patch including a first area and a second area, in which a microneedle is formed, and including at least one enzyme configured to react with a body fluid of a user and configured to measure a blood glucose level in the body fluid extracted from the second area using light sources and a photodetector includes operating the light source to emit light beams toward the first area and the second area, receiving a first reflected light beam reflected from the first area and a second reflected light beam reflected from the second area among the emitted light beams and measuring any one of wavelengths and intensity changes of the first reflected light beam and the second reflected light beam, analyzing data obtained by measuring the second reflected light beam and calculating a blood glucose level, and analyzing data obtained by measuring the first reflected light beam and correcting the calculated blood glucose level on the basis of a result of analyzing.

BRIEF DESCRIPTION OF DRAWINGS

Example embodiments of the present invention will become more apparent by describing in detail example embodiments of the present invention with reference to the accompanying drawings, in which.

DESCRIPTION OF EXAMPLE EMBODIMENTS

Figure 1:
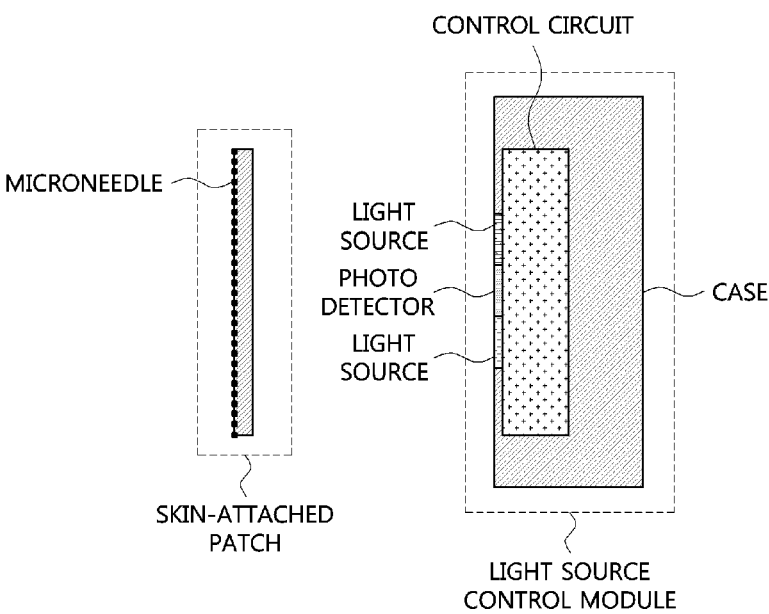
FIG. 1 is a side cross-sectional view of a conventional blood glucose level measurement apparatus.

Since the present invention may be variously modified and have a variety of embodiments, particular embodiments will be illustrated in the drawings and described in detail hereinafter. However, these are not intended to limit the present invention to a particularly disclosed form and it should be understood that the present invention includes all changes, equivalents, and substitutes included within the concept and technical scope of the present invention. In a description of each drawing, like elements will be referred to as like reference numerals.

It will be understood that, although the terms first, second, A, B, etc. may be used herein to describe various elements, these elements should not be limited by these terms. These terms are only used to distinguish one element from another. For example, a first element could be termed a second element, and, similarly, a second element could be termed a first element, without departing from the scope of the present invention. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (i.e., "between" versus "directly between," "adjacent" versus "directly adjacent," etc.).

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, exemplary embodiments of the present invention will be described in more detail with reference to the attached drawings. In the description of the present invention, to facilitate overall understanding, in the drawings, like elements are referred to as like reference numerals. Also, a repetitive description of the same elements will be omitted.

Figure 2:
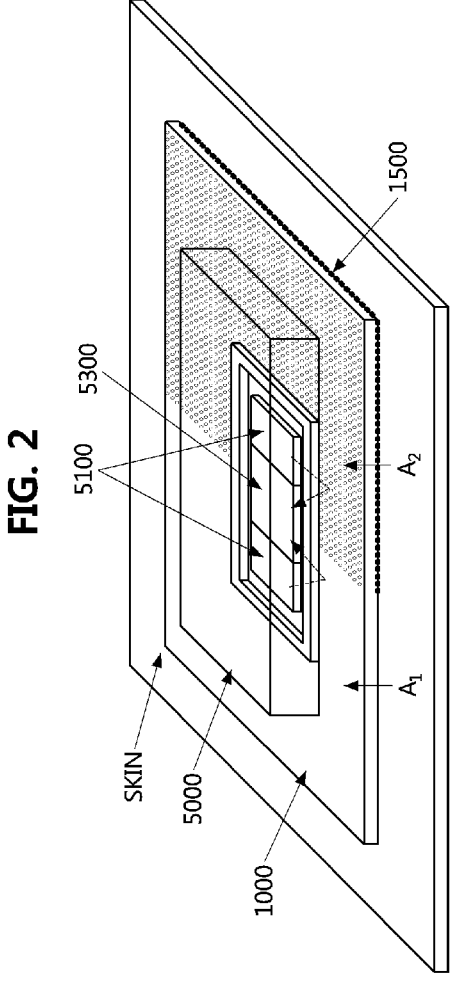
FIG. 2 is a perspective view of a blood glucose level measurement apparatus according to example embodiments of the present invention.

FIG. 2 is a perspective view of a blood glucose level measurement apparatus according to example embodiments of the present invention.

Referring to FIG. 2, a blood glucose level measurement apparatus 5000 is an apparatus configured to measure a blood glucose level of body fluid of a user which is extracted by a patch 1000. Here, for a definite description of the patch 1000, components of a memory 5500 will be omitted.

According to embodiments, the blood glucose level measurement apparatus may be provided with the patch 1000 integrally or provided separately.

As described above, the patch 1000 is a component configured to extract the body fluid of the user and may be provided to have a certain-sized pad shape.

According to embodiments, an adhesive material may be applied to one surface of the patch 1000. Accordingly, the patch 1000 may be attached to the skin of the user.

The patch 1000 may include at least one enzyme. Here, the enzyme dispersed in the patch 1000 may react with glycation products in blood. Here, glycation products may be a material formed by coupling proteins with glucose in the body fluid due to glycation.

The patch 1000 may generate advanced glycation endproducts (AGEs) through glycation between the body fluid and the enzyme. Accordingly, a blood glucose level measurement apparatus 5000 which will be described below may analyze light reflected by the patch 1000 and calculate concentration of AGEs so as to measure a blood glucose level of the user.

A method of measuring the concentration of AGEs will be described in detail in a description of components of the blood glucose level measurement apparatus 5000.

Figure 3:
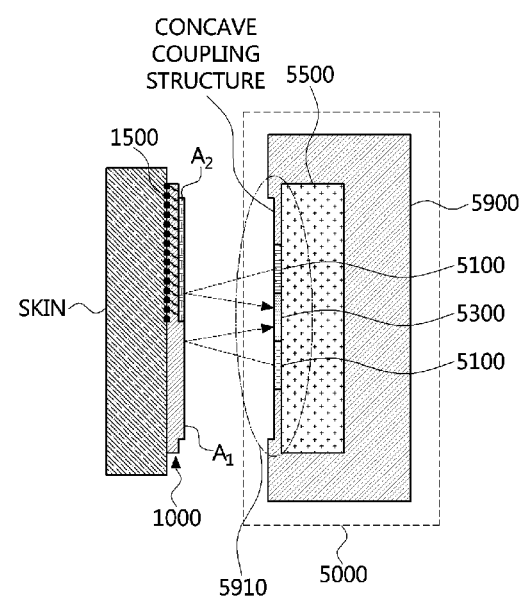
FIG. 3 is a side cross-sectional view illustrating a patch and the blood glucose level measurement apparatus according to example embodiments of the present invention.

FIG. 3 is a side cross-sectional view illustrating the patch and the blood glucose level measurement apparatus according to example embodiments of the present invention.

Referring to FIGS. 2 and 3, the patch 1000 may include a first area A1 and a second area A2. Here, the first area A1 may be a comparative area provided to correct an error of a blood glucose level when the blood glucose level measurement apparatus 5000 measures reflected light.

In more detail, in comparison to the second area A2 which will be described below, the first area A1 has a difference that a microneedle 1500 is not formed on one surface but may have the same environmental factors. Accordingly, even when the patch 1000 is attached to the skin of the user, the body fluid of the user is not extracted from the first area A1.

In other words, in the first area A1 of the patch 1000, an enzyme reaction caused by extraction may not occur. Accordingly, the blood glucose level measurement apparatus 5000 may utilize data obtained by measuring light reflected from the first area A1 which is received by a photodetector as a correction value of data obtained by measuring reflected light which is received from the second area A2.

A method of calculating a blood glucose level utilizing data obtained by analyzing the reflected light from the first area A1 as a correction value will be described in detail in the following description of the blood glucose level measurement apparatus 5000.

The second area A2 may be an area from which the body fluid of the user is extracted when the patch 1000 is attached to the skin of the user. In other words, the second area A2 may be an area from which the body fluid of the user is collected.

In more detail, on one surface of the second area A2, at least one microneedle 1500 may be formed to protrude.

Accordingly, in the second area A2, as described above, when the patch 1000 is attached to the skin of the user, the body fluid of the user may be extracted using the at least one microneedle 1500.

Accordingly, the extracted body fluid may react with the at least one enzyme in the patch 1000 as described above. The microneedle 1500 will be described below in detail with reference to FIG. 4.

Figure 4:
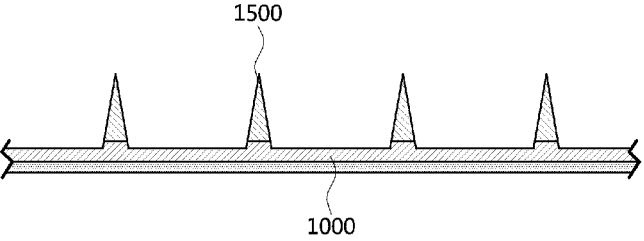
FIG. 4 is a cross-sectional view illustrating a microneedle in the patch according to example embodiments of the present invention.

FIG. 4 is a cross-sectional view illustrating the microneedle in the patch according to example embodiments of the present invention.

Referring to FIG. 4, the microneedle 1500 may be formed to protrude at a certain length from one surface of the patch 1000.

According to embodiments, the microneedle 1500 may have a conic shape with a pointed needle formed on one end of the microneedle 1500. Accordingly, when the one surface of the patch 1000 is attached to the skin of the user, the microneedle 1500 may penetrate into skin tissue of the user and extract the body fluid of the user. For example, the microneedle 1500 may be provided to be several micro meters (m).

However, the microneedle 1500 according to the example embodiments of the present invention may not be limited to the above embodiment and may have a variety of shapes for easy extraction.

Referring back to FIG. 2, the body fluid of the user which is extracted using the microneedle 1500 may be absorbed by the patch 1000. Accordingly, the body fluid of the user may react with the enzyme dispersed in the patch 1000.

In brief, the patch 1000 according to the example embodiments of the present invention may extract a minimum amount of the body fluid using the microneedle 1500 so as to prevent an error caused by spreading of the body fluid extracted in the second area A2 when the blood glucose level measurement apparatus 5000 analyzes a blood glucose level. Accordingly, the blood glucose level measurement apparatus capable of measuring a blood glucose level with high precision and high reliability may be provided.

Subsequently, the blood glucose level measurement apparatus 5000 may measure a blood glucose level of the user by measuring and analyzing concentration of the AGEs from the body fluid of the user which is extracted from the second area A2 of the patch 1000.

Hereinafter, the blood glucose level measurement apparatus 5000 will be described in detail for each component.

Figure 5:
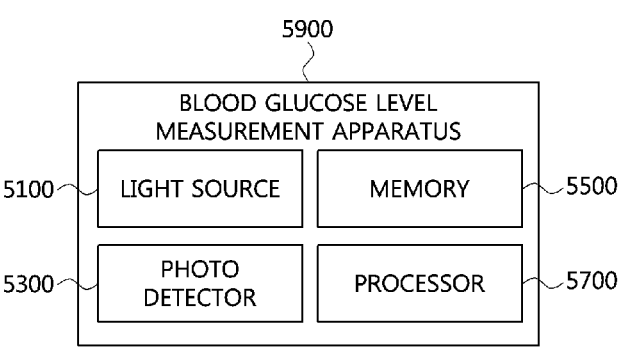
FIG. 5 is a block diagram of the blood glucose level measurement apparatus according to example embodiments of the present invention.

FIG. 5 is a block diagram of the blood glucose level measurement apparatus according to example embodiments of the present invention.

Referring to FIGS. 2 and 5, the blood glucose level measurement apparatus 5000 may measure a wavelength and an intensity level of light emitted from the enzyme in the patch 1000 as described above.

In more detail, the blood glucose level measurement apparatus 5000 may include a light source 5100, a photodetector 5300, the memory 5500, a processor 5700, and a case 5900.

The light source 5100 may emit light toward the patch 1000 as described above. For example, the light source 5100 may be a light emitting diode (LED).

According to embodiments, a plurality of such light sources 5100 may be provided. For example, the plurality of light sources 5100 may be located at one place in the blood glucose level measurement apparatus 5000. Here, a position of the light sources 5100 may be determined in consideration of positions of the photodetector 5300 which will be described below and the first area A1 and the second area A2 of the patch 1000.

In more detail, the plurality of light sources 5100 may be disposed at places where light beams separately emitted toward the first area A1 and the second area A2 are reflected by the enzyme in the patch 1000 such that final paths of the reflected light beams face the photodetector 5300. In other words, the plurality of light sources 5100 may be separately located in places where a first reflected light beam reflected from the first area A1 and second reflected light beams reflected from the second area A2 of the patch 1000 are receivable by the photodetector 5300. For example, the plurality of light sources 5100 may be arranged on both sides on the basis of the photodetector 5300 located in a central part of the blood glucose level measurement apparatus 5000.

The photodetector 5300 may measure light reflected from the patch 1000 as described above.

In more detail, the photodetector 5300 may measure a wavelength and an intensity change of each of the first reflected light beam reflected from the first area A1 and the second reflected light beams reflected from the second area A2 of the patch 1000. Subsequently, the photodetector 5300 may transmit first measurement data obtained by measuring the wavelength and the intensity change of the first reflected light beam and second measurement data obtained by measuring the wavelength and the intensity change of the second reflected light beam to the memory 5500.

The memory 5500 may temporarily store one or more of first measurement data and second measurement data which are received from the photodetector 5300. Accordingly, the processor 5700 which will be described below may calculate a blood glucose level of the user by analyzing the second measurement data which is temporarily stored in the memory 5500 and may correct the calculated blood glucose level using the first measurement data.

In more detail, the memory 5500 may include one or more instructions for executing the processor 5700.

According to embodiments, the one or more instructions may include an instruction for operating at least one of the light sources 5100 to emit light beams toward the first area A1 and the second area A2, an instruction for receiving, by the photodetector 5300, the first reflected light beam reflected from the first area A1 and the second reflected light beam from the second area A2 among the emitted light beams so as to measure wavelengths and intensity levels of the first reflected light beam and the second reflected light beam, an instruction for calculating a blood glucose level by analyzing data obtained by measuring the second reflected light beam, and an instruction for analyzing data obtained by measuring the first reflected light beam and correcting the blood glucose level on the basis of a result of analyzing.

The processor 5700 may execute the one or more instructions in the memory 5500. Operations of the processor 5700 executing the one or more instructions will be described in detail in a description of a method of measuring a blood glucose level which will be described below.

The case 5900 may accommodate at least one of the light sources 5100 and the photodetector 5300. The case 5900 will be described in detail with reference to FIG. 6.

Figure 6:
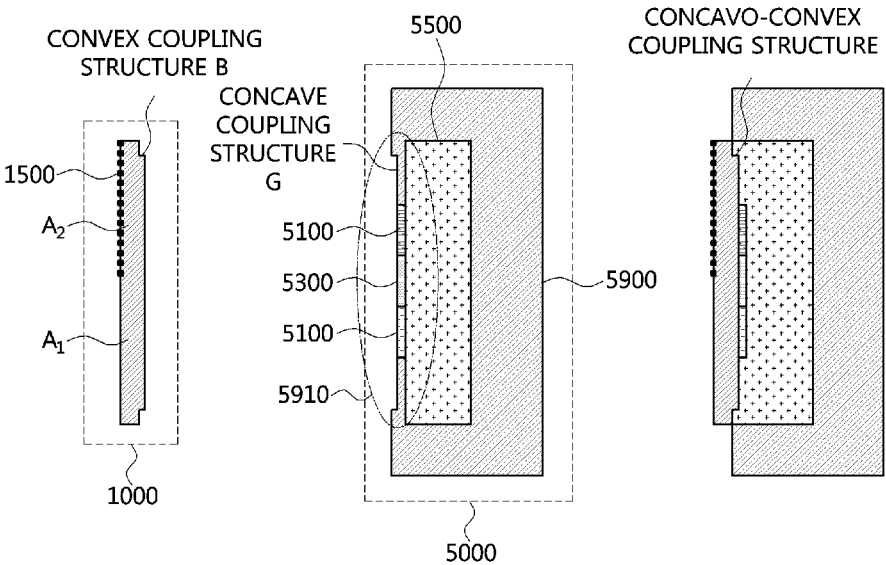
FIG. 6 is a side cross-sectional view illustrating a case of the blood glucose level measurement apparatus according to example embodiments of the present invention.

FIG. 6 is a side cross-sectional view illustrating the case of the blood glucose level measurement apparatus according to example embodiments of the present invention.

Referring to FIG. 6, the case 5900 may include an opening portion 5910 in one surface thereof. Accordingly, the light source 5100 and the photodetector 5300 may be disposed so that a light emission portion of the light source 5100 and a light reception portion of the photodetector 5300 are located in the opening portion 5910.

According to embodiments, in the case 5900, the plurality of light sources 5100 and the photodetector 5300 may be included. Here, the light reception portion of the photodetector 5300 may be located in the opening portion 5910 of the case 5900, and the light emission portions of the plurality of light sources 5100 may be located on both sides on the basis of the receiving portion of the photodetector 5300. Accordingly, when the blood glucose level measurement apparatus 5000 is coupled to the patch 1000, light output by the light emission portion of the light source 5100 may be emitted toward the other surface of the patch 1000 and the light reception portion of the photodetector 5300 may receive light reflected by reaction of the enzyme and glycation products in the patch 1000.

The case 5900 may be coupled to the other surface of the patch 1000 as described above. According to embodiments, the patch 1000 and the case 5900 may be bound by unevenness. A binding structure between the patch 1000 and the case 5900 using the unevenness will be described below in detail.

A fixing groove G having a concave structure and a fixing protrusion B having a convex structure may be formed on the other surface of the patch 1000 and the one surface of the case 5900 or vice versa so as to be bound to each other.

Here, a diameter of the fixing protrusion B may correspond to a width of the fixing groove G. Accordingly, adhesion and fixing force of the patch 1000 and the case 5900 may be improved when being coupled to each other.

According to one embodiment, one or more fixing grooves G having a concave structure may be formed in one surface of the case 5900 and one or more fixing protrusions B having a convex structure may be formed on the other surface of the patch 1000.

Hereinafter, embodiments of the fixing protrusion B having a convex structure and formed on the other surface of the patch 1000 and the fixing groove G having a concave structure and formed in the one surface of the case 5900 will be described in detail with reference to FIGS. 7 to 9.

Figure 7:
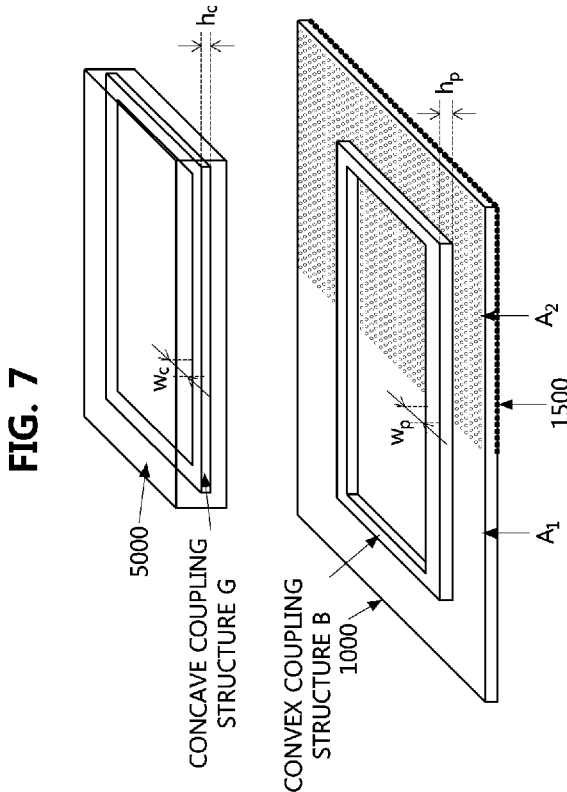
FIG. 7 is a perspective view illustrating a binding structure of the blood glucose level measurement apparatus according to one embodiment of the present invention.

FIG. 7 is a perspective view illustrating a binding structure of the blood glucose level measurement apparatus according to one embodiment of the present invention.

Referring to FIG. 7, the fixing protrusion B having a convex structure and having a certain height $h_p$ may be formed on the other surface of the patch 1000.

According to embodiments, the fixing protrusion B may be formed on the other surface of the patch 1000 to protrude in a quadrangular frame shape.

Also, the fixing groove G having a concave structure in a quadrangular frame shape having a certain depth $h_c$ corresponding to the fixing protrusion B formed on the other surface of the patch 1000 may be formed in the one surface of the case 5900.

Here, as described above, since the fixing protrusion B on the patch 1000 and the fixing groove G in the case 5900 have heights $h_p$ and $h_c$ and widths $W_p$ and $W_c$ which correspond to each other, coupling adhesion between the patch 1000 and the case 5900 may be improved.

Figure 8:
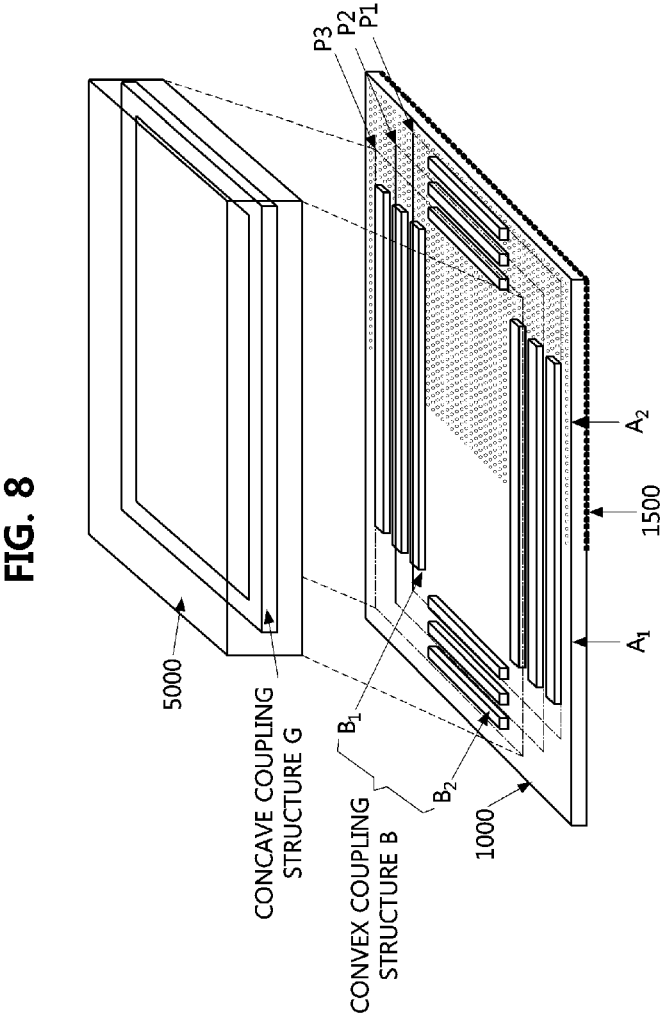
FIG. 8 is a perspective view illustrating a binding structure of the blood glucose level measurement apparatus according to a first embodiment of the present invention.

FIG. 8 is a perspective view illustrating a binding structure of the blood glucose level measurement apparatus according to a first embodiment of the present invention.

Referring to FIG. 8, the fixing protrusion B formed on the other surface of the patch 1000 may be provided as one or more bars having a certain length.

According to embodiments, the fixing protrusion B may include a first fixing protrusion B1 located on a first axis of the patch 1000 and a second fixing protrusion B2 located on a second axis perpendicular to the first axis. Here, lengths of the first fixing protrusion B1 and the second fixing protrusion B2 may be adjusted according to a shape of the patch 1000 and pluralities of such first fixing protrusions B1 and second fixing protrusions B2 may be arranged.

Meanwhile, like one embodiment of the present invention in accordance with FIG. 5, the fixing groove G having a quadrangular frame shape may be formed on one surface of the case 5900.

Accordingly, when the patch 1000 and the case 5900 are coupled to each other, the fixing groove G of the case 5900 may be coupled to the other surface of the patch 1000 freely in shapes P1 to P3.

In other words, since the blood glucose level measurement apparatus 5000 according to example embodiments of the present invention is freely coupled to the patch 1000, in which the plurality of fixing protrusions B are arranged, regardless of a size of the patch, positions of the light sources and the photodetector, a size of the blood glucose level measurement apparatus 5000, or the like, reflected light beams may be detected with high precision and high convenience.

Figure 9:
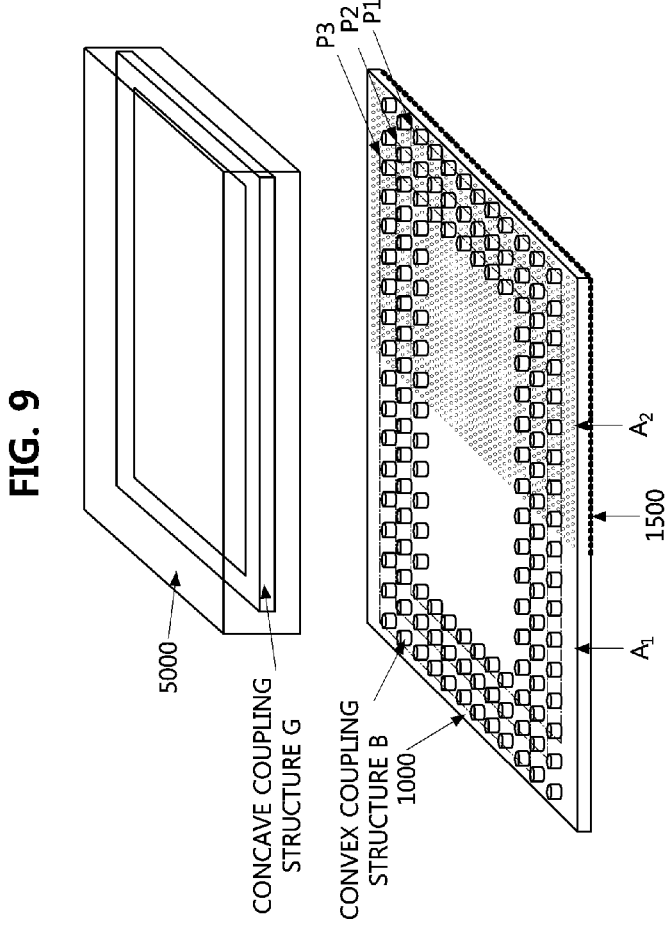
FIG. 9 is a perspective view illustrating a binding structure of the blood glucose level measurement apparatus according to a second embodiment of the present invention.

FIG. 9 is a perspective view illustrating a binding structure of the blood glucose level measurement apparatus according to a second embodiment of the present invention.

Referring to FIG. 9, the fixing protrusion B formed on the other surface of the patch 1000 may be provided to have a cylindrical protrusion shape having a certain diameter.

According to embodiments, a plurality of such cylindrical fixing protrusions B may be arranged on the patch 1000.

Meanwhile, like one embodiment of the present invention in accordance with FIG. 6, the fixing groove G having a quadrangular frame shape with a certain depth may be formed on one surface of the case 5900.

Accordingly, as shown in FIG. 7, the fixing groove G of the case 5900 may be freely coupled to the other surface of the patch 1000 in shapes P1 to P3.

Figure 10:
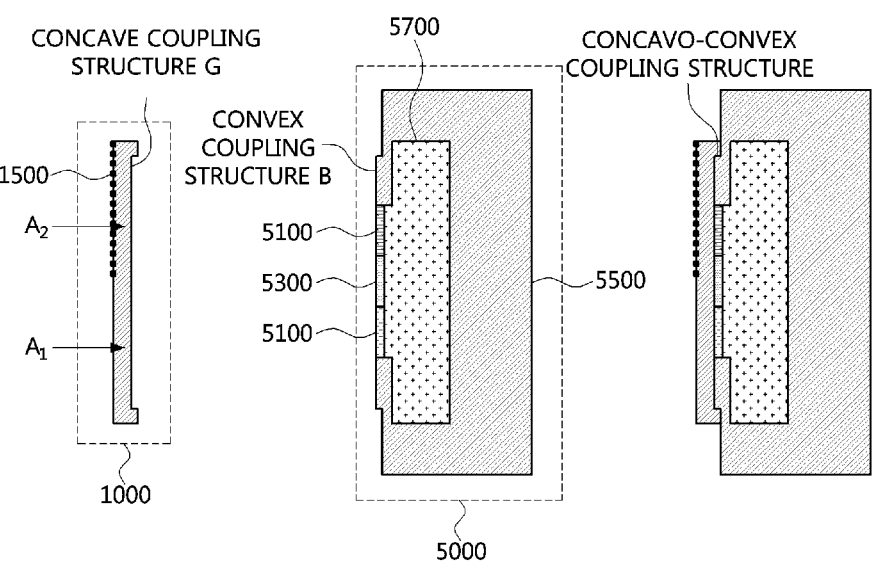
FIG. 10 is a side cross-sectional view illustrating a binding structure of the blood glucose level measurement apparatus according to another embodiment of the present invention.

FIG. 10 is a side cross-sectional view illustrating a binding structure of the blood glucose level measurement apparatus according to another embodiment of the present invention.

Referring to FIG. 10, one or more fixing protrusions B having a convex structure may be formed in one surface of the case 5900 and one or more fixing grooves G having a concave structure may be formed on the other surface of the patch 1000.

Hereinafter, embodiments of the fixing protrusion B having a convex structure and formed on the one surface of the case 5900 and the fixing groove G having a concave structure and formed in the other surface of the patch 1000 will be described in detail with reference to FIGS. 11 to 12.

Figure 11:
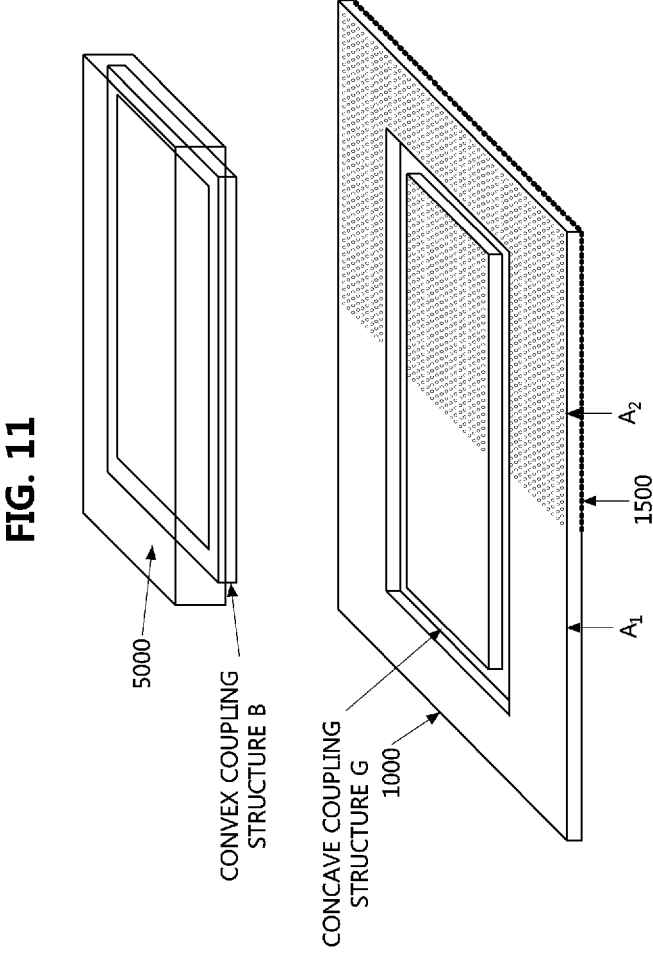
FIG. 11 is a perspective view illustrating a binding structure of the blood glucose level measurement apparatus according to a third embodiment of the present invention.

FIG. 11 is a perspective view illustrating a binding structure of the blood glucose level measurement apparatus according to a third embodiment of the present invention.

Referring to FIG. 11, the fixing groove G having a quadrangular frame shape with a certain depth may be formed in the other surface of the patch 1000.

Also, the fixing protrusion B corresponding to the fixing groove G formed in the other surface of the patch 1000 and having a certain height may be formed on one surface of the case 5900.

Here, as described above with reference to FIG. 7, since the fixing groove G formed in the other surface of the patch 1000 and the fixing protrusion B formed on the one surface of the case 5900 have a height and a width corresponding to each other, respectively, coupling adhesion between the patch 1000 and the case 5900 may be improved.

Figure 12:
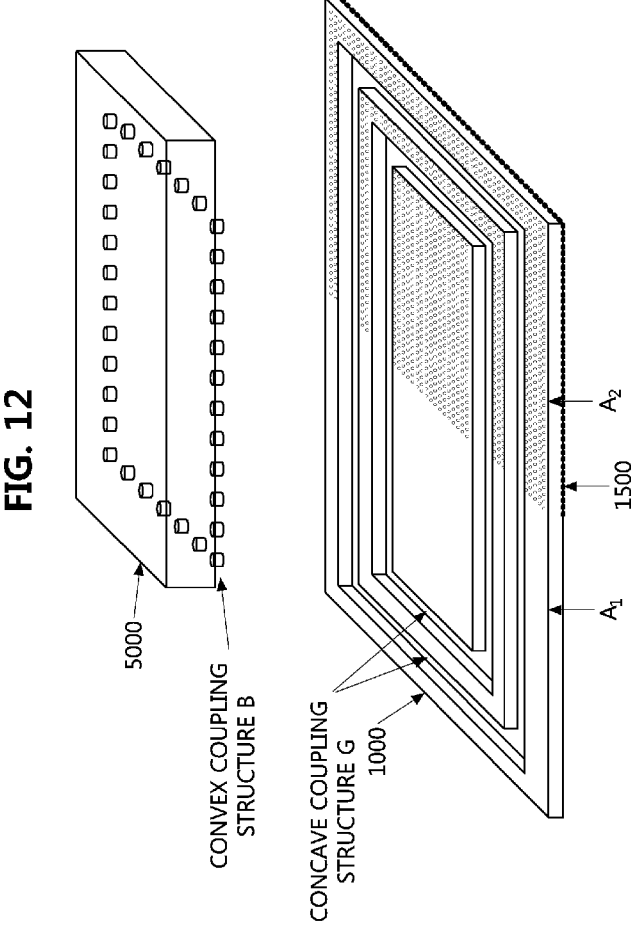
FIG. 12 is a perspective view illustrating a binding structure of the blood glucose level measurement apparatus according to a fourth embodiment of the present invention.

FIG. 12 is a perspective view illustrating a binding structure of the blood glucose level measurement apparatus according to a fourth embodiment of the present invention.

Referring to FIG. 12, the fixing groove G formed on the other surface of the patch 1000 may be provided to have a quadrangular frame shape having a certain depth.

According to embodiments, a plurality of fixing groove G may be provided on the other surface of the patch 1000 while the fixing groove G having the quadrangular frame shape with a size gradually increasing toward an outer edge of the patch 1000 may be provided.

Meanwhile, cylindrical protrusions B having a certain diameter may be formed on one surface of the case 5900.

According to embodiments, the cylindrical fixing protrusions B may be inserted into and bound to one or more of a plurality of such fixing grooves G arranged on the other surface of the patch 1000.

Accordingly, since the blood glucose level measurement apparatus 5000 according to the present invention may be fixed to the other surface of the patch 1000 with high adhesion and freely coupled thereto regardless of a size of the patch, positions of the light sources and the photodetector, a size of the blood glucose level measurement apparatus 5000, or the like, reflected light beams may be detected with high precision and high convenience.

In the above, the blood glucose level measurement apparatus according to example embodiments of the present invention has been described. Hereinafter, a blood glucose level measurement method using the blood glucose level measurement apparatus will be described.

Figure 13:
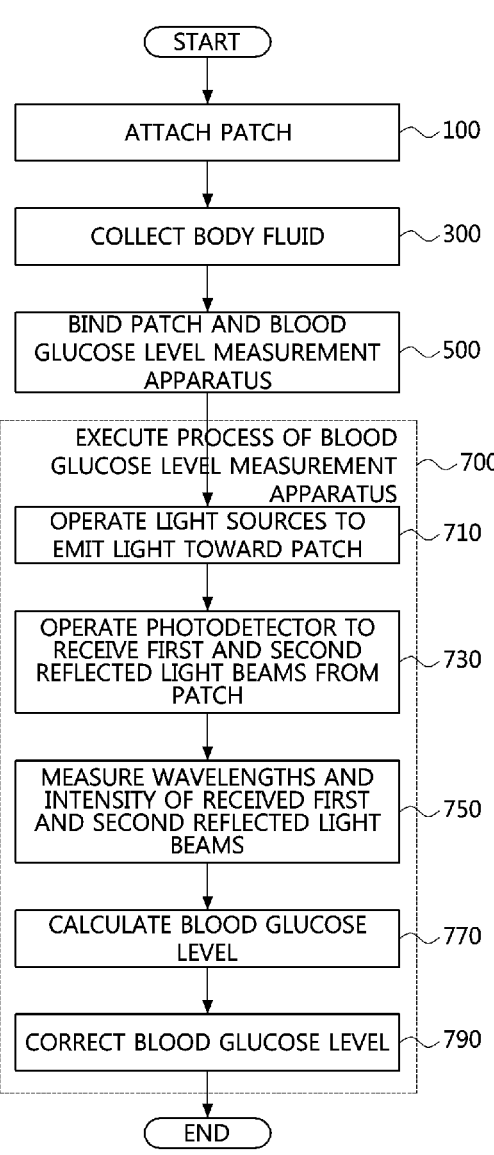
FIG. 13 is a flowchart illustrating a blood glucose level measurement method according to example embodiments of the present invention.

FIG. 13 is a flowchart illustrating a blood glucose level measurement method according to example embodiments of the present invention.

Referring to FIG. 13, a user may attach the patch 1000 to a part of the user's body (100). Here, the user may attach the patch 1000 so that one surface of the patch 1000, on which one or more microneedles 1500 are formed, faces the body. Subsequently, the blood glucose level measurement apparatus may collect a body fluid (300). In other words, the blood glucose level measurement apparatus may extract the body fluid from the user.

When body fluid is completely collected, the blood glucose level measurement apparatus 5000 may be bound to the patch 1000 (500). Subsequently, the processor 5700 of the blood glucose level measurement apparatus 5000 may be executed (700).

In a more detailed description of execution of the processor 5700, the processor 5700 may execute the light source 5100 to emit light toward the patch 1000 (710).

According to embodiments, the processor 5700 may operate the plurality of light sources 5100 to emit light toward the first area A1 and the second area A2 of the patch 1000.

Subsequently, the processor 5700 may execute the photodetector 5300 to receive the light reflected by the patch 1000 (730).

In more detail, the processor 5700 may separately measure wavelengths and intensity levels of a first reflected light beam reflected from the first area A1 and second reflected light beams reflected from the second area A2 of the patch 1000 using the photodetector 5300 (750).

The processor 5700 may calculate a blood glucose level by analyzing second measurement data obtained by measuring the wavelength and the intensity level of the second reflected light beam (770).

Subsequently, the processor 5700 may analyze first measurement data obtained by measuring the wavelength and the intensity level of the first reflected light beam and correct an error of the calculated blood glucose level (790). In other words, the processor 5700 may calculate a blood glucose level with an error being corrected by using first analysis data of the first light beam received from the first area A1 of the patch 1000 and correcting second analysis data of the second reflected light beam received from the second area A2.

The blood glucose level measurement method according to example embodiments of the present invention may be provided to have high precision and high reliability in consideration of environmental factors capable of influencing measured values of the first and second reflected light beams such as a skin color of the user, an intensity level of the light source, and the like by correcting an error of an obtained blood glucose level by analyzing data obtained by measuring the second reflected light beam received from the second area A2 on the basis of data obtained by measuring the first reflected light beam received from the first area A1.

In the above, the blood glucose level measurement apparatus and method according to example embodiments of the present invention have been described.

In the blood glucose level measurement apparatus and method according to example embodiments of the present invention, the apparatus coupled to a patch with a microneedle formed in at least one area and configured to calculate a blood glucose level of a body fluid extracted from a user may calculate the blood glucose level by analyzing a reflected light beam reflected from the patch with a microneedle formed in a second area and correct the calculated blood glucose level of the user by analyzing data obtained by measuring a reflected light beam from a first area from which the body fluid is not extracted so as to measure a precise blood glucose level with an error being reduced in consideration of environmental factors influencing measurement. Also, unevennessses corresponding to each other may be formed on one surface of a case and the other surface of the patch for binding with high adhesion so that a light leakage phenomenon may be prevented while light beams are emitted from the light sources toward the patch and reflected light beams from the patch are measured by a photodetector so as to measure a blood glucose level with high precision, high efficiency, and high reliability.

The operations of the method according to example embodiments of the present invention may be implemented as a computer-readable program or codes in a computer-readable recording medium. The computer-readable recording medium includes all types of recording media in which data readable by a computer system is stored. Also, in the computer-readable recording medium, a program or codes, which are distributed in a computer system connected through a network and readable using a distribution method may be stored and executed.

Also, the computer-readable recording medium may include hardware devices such as a read-only memory (ROM), a random-access memory (RAM), a flash memory, and the like which are particularly configured to store and execute program instructions. Program instructions may include not only machine language codes formed by a compiler but also high-level language codes executable by a computer using an interpreter or the like.

Although some aspects of the present invention have been described in the context of the device, they may correspond to the method. Here, blocks or the device corresponds to operations of the method or features of the operations. Likewise, aspects described in the context of the method may feature corresponding blocks or items or the device. Some or all of the operations of the method may be performed by (or using) a hardware device, for example, a microprocessor, a programmable computer, or an electronic circuit. In some embodiments, one or more of the most significant operations of the method may be performed by the above device.

In embodiments, a programmable logic device (for example, a field programmable gate array) may be used to perform some or all of functions of the above-described methods. In the embodiments, the field programmable gate array may operate with a microprocessor configured to perform one of the above-described methods. Generally, the methods may be performed by a certain hardware device.

In the blood glucose level measurement apparatus and method according to example embodiments of the present invention, a blood glucose level of a user may be calculated by analyzing a reflected light beam reflected from a patch with a microneedle formed in a second area and the calculated blood glucose level may be corrected by analyzing data obtained by measuring a reflected light beam from a first area from which the body fluid is not extracted so as to measure a precise blood glucose level with an error being reduced in consideration of environmental factors influencing measurement. Also, unevennessses corresponding to each other may be formed on one surface of a case and the other surface of the patch for binding with high adhesion so that a light leakage phenomenon may be prevented while light beams are emitted from the light sources toward the patch and reflected light beams from the patch are measured by a photodetector so as to measure a blood glucose level with high precision, high efficiency, and high reliability.

While the present invention has been described with reference to exemplary embodiments, it will be understood by those skilled in the art that variations and modifications of the invention may be made without departing from the spirit and scope of the invention as defined by the appended claims.

What is claimed is:

1. A blood glucose level measurement apparatus for measuring a blood glucose level in a human body, the apparatus comprising:
a patch comprising a first region and continuous second region on one surface, wherein the second region is integrally formed and continuously defined in a predetermined portion of the one surface, and a plurality of microneedles comprising at least one enzyme configured to react with a body fluid of a user and said plurality of microneedles being collectively arranged within the second region, wherein no microneedle is formed on the first region; and
a light source control module coupled to the patch and configured to calculate a blood glucose level of the body fluid that is extracted from the user,
wherein the light source control module comprises:
a plurality of light sources configured to emit light toward an opposite surface to the one surface, the plurality of light sources emitting light toward the first region and the second region of the one surface;
a photodetector configured to detect a first light reflected from the first region and a second light reflected from the second region; and
a case configured to accommodate the light sources and the photodetector,
wherein at least one fixing protrusion is formed on one of the opposite surface of the patch and one surface of the case, and at least one fixing groove is formed on the other one of the opposite surface of the patch and the one surface of the case, and
wherein the light source control module is attached to the patch via a concave-convex structure formed by the at least one fixing protrusion and the at least one fixing groove.

2. The apparatus of claim 1, wherein a height of the at least one fixing protrusion corresponds to a depth of the at least one fixing groove.

3. The apparatus of claim 2, wherein the at least one fixing protrusion is formed on the opposite surface of the patch, and
wherein the at least one fixing groove is formed on the one surface of the case.

4. The apparatus of claim 3, wherein the fixing protrusion is provided to have a cylindrical shape having a certain diameter,
wherein the fixing groove has a width corresponding to the diameter of the fixing protrusion.

5. The apparatus of claim 3, wherein the fixing protrusion and the fixing groove have quadrangular frame shapes with certain widths.

6. The apparatus of claim 3, wherein the at least one fixing protrusion is provided in the form of a bar with a predetermined width, and
wherein the at least one fixing groove has a rectangular frame shape with a width corresponding to the width of the fixing protrusion.

7. The apparatus of claim 3, wherein when a plurality of fixing protrusions are arranged on the opposite surface of the patch, the at least one fixing groove is configured to engage with the plurality of fixing protrusions.

8. The apparatus of claim 2, wherein the at least one fixing groove is formed on the opposite surface of the patch, and the at least one fixing protrusion is formed on the one surface of the case.

9. The apparatus of claim 8, wherein the at least one fixing groove is provided in the form of a linearly extended portion with a predetermined width, and
wherein the at least one fixing protrusion has in the form of a bar with a width corresponding to the width of the at least one fixing groove.

10. The apparatus of claim 8, wherein when a plurality of fixing grooves are arranged on the opposite surface of the patch, the at least one fixing protrusion is configured to engage with any one of the plurality of fixing grooves.

11. The apparatus of claim 1, wherein the photodetector measures wavelengths and intensity changes of the first reflected light and the second reflected light.

12. The apparatus of claim 11, wherein the photodetector calculates a blood glucose level by analyzing data obtained by measuring the second reflected light and corrects the calculated blood glucose level on the basis of a result of analyzing data obtained by measuring the first reflected light.

13. The apparatus of claim 11, wherein the plurality of light sources comprise a first light source and a second light source,
wherein the first light source is positioned such that a path of the first reflected light leads to the photodetector, and
wherein the second light source is positioned such that a path of the second reflected light leads to the photodetector.

* * * * *